United States Patent
Park

(10) Patent No.: US 8,502,867 B2
(45) Date of Patent: Aug. 6, 2013

(54) SYNTHETIC APERTURE OPTICS IMAGING METHOD USING MINIMUM SELECTIVE EXCITATION PATTERNS

(75) Inventor: Jong Buhm Park, Sunnyvale, CA (US)

(73) Assignee: LightSpeed Genomics, Inc., Santa Clara, CA (US)

( * ) Notice: Subject to any disclaimer, the term of this patent is extended or adjusted under 35 U.S.C. 154(b) by 748 days.

(21) Appl. No.: 12/728,110

(22) Filed: Mar. 19, 2010

(65) Prior Publication Data

US 2011/0228068 A1     Sep. 22, 2011

(51) Int. Cl.
*H04N 9/47* (2006.01)

(52) U.S. Cl.
USPC ........................ 348/135; 348/79; 348/80

(58) Field of Classification Search
USPC .................................. 348/135, 79, 80
See application file for complete search history.

(56) References Cited

U.S. PATENT DOCUMENTS

| | | |
|---|---|---|
| 3,780,217 A | 12/1973 | Sawatari |
| 3,785,262 A | 1/1974 | Stroke |
| 5,041,733 A | 8/1991 | Noguchi et al. |
| 5,086,341 A | 2/1992 | Tamada et al. |
| 5,341,312 A | 8/1994 | Lisson et al. |
| 5,406,412 A | 4/1995 | Zehnpfennig et al. |
| 5,470,710 A | 11/1995 | Weiss et al. |
| 5,511,060 A | 4/1996 | Jau-Jiu et al. |
| 5,674,698 A | 10/1997 | Zarling et al. |
| 5,695,934 A | 12/1997 | Brenner |
| 5,750,341 A | 5/1998 | Macevicz |
| 5,751,243 A | 5/1998 | Turpin |
| 5,763,175 A | 6/1998 | Brenner |
| 5,780,231 A | 7/1998 | Brenner |
| 5,902,723 A | 5/1999 | Dower et al. |
| 5,969,119 A | 10/1999 | Macevicz |
| 6,013,445 A | 1/2000 | Albrecht et al. |
| 6,016,196 A | 1/2000 | Mermelstein |
| 6,140,660 A * | 10/2000 | Mermelstein ............... 250/550 |
| 6,306,597 B1 | 10/2001 | Macevicz |
| 6,406,848 B1 | 6/2002 | Bridgham et al. |
| 6,525,875 B1 * | 2/2003 | Lauer ......................... 359/371 |

(Continued)

FOREIGN PATENT DOCUMENTS

| | | |
|---|---|---|
| KR | 10-2000-0004675 | 1/2000 |
| WO | WO 2009/032510 | 3/2009 |

OTHER PUBLICATIONS

Title: "Resolution Improvement in Optical Microscopy by use of multi-beam interferometric illumination" Author: Jekwan Ryu Date: Sep. 2003.*

(Continued)

*Primary Examiner* — Mehrdad Dastouri
*Assistant Examiner* — Jared Walker
(74) *Attorney, Agent, or Firm* — Fenwick & West LLP

(57) ABSTRACT

A synthetic aperture optics (SAO) imaging method minimizes the number of selective excitation patterns used to illuminate the imaging target, based on the objects' physical characteristics corresponding to spatial frequency content from the illuminated target and/or one or more parameters of the optical imaging system used for SAO. With the minimized number of selective excitation patterns, the time required to perform SAO is reduced dramatically, thereby allowing SAO to be used with DNA sequencing applications that require massive parallelization for cost reduction and high throughput. In addition, an SAO apparatus optimized to perform the SAO method is provided. The SAO apparatus includes a plurality of interference pattern generation modules that can be arranged in a half-ring shape.

27 Claims, 11 Drawing Sheets

U.S. PATENT DOCUMENTS

| | | | |
|---|---|---|---|
| 6,539,805 | B2 | 4/2003 | Heaslip et al. |
| 6,548,820 | B1 | 4/2003 | Mermelstein |
| 6,654,505 | B2 | 11/2003 | Bridgham et al. |
| 6,787,308 | B2 | 9/2004 | Balasubramanian et al. |
| 6,806,052 | B2 | 10/2004 | Bridgham et al. |
| 6,831,994 | B2 | 12/2004 | Bridgham et al. |
| 6,833,246 | B2 | 12/2004 | Balasubramanian |
| 6,911,345 | B2 | 6/2005 | Quake et al. |
| 6,969,488 | B2 | 11/2005 | Bridgham et al. |
| 7,115,400 | B1 | 10/2006 | Adessi et al. |
| 7,122,384 | B2 | 10/2006 | Prober et al. |
| 7,169,560 | B2 | 1/2007 | Lapidus et al. |
| 7,211,390 | B2 | 5/2007 | Rothberg et al. |
| 7,248,338 | B2 | 7/2007 | Fukuda |
| 7,397,018 | B1 * | 7/2008 | Pham et al. ............. 250/201.9 |
| 7,405,114 | B2 | 7/2008 | Oishi |
| 7,602,501 | B2 | 10/2009 | Ralston et al. |
| 7,639,909 | B2 | 12/2009 | Murshid et al. |
| 7,916,144 | B2 | 3/2011 | Schiwietz et al. |
| 8,329,560 | B2 | 12/2012 | Lee et al. |
| 2002/0051992 | A1 | 5/2002 | Bridgham et al. |
| 2002/0061529 | A1 | 5/2002 | Bridgham et al. |
| 2002/0137052 | A1 | 9/2002 | Bridgham et al. |
| 2003/0077615 | A1 | 4/2003 | Bridgham et al. |
| 2003/0224419 | A1 | 12/2003 | Corcoran et al. |
| 2005/0099682 | A1 | 5/2005 | Lauer |
| 2005/0100932 | A1 | 5/2005 | Lapidus et al. |
| 2005/0221351 | A1 | 10/2005 | Ryu |
| 2005/0239113 | A1 | 10/2005 | Ryu et al. |
| 2005/0239114 | A1 | 10/2005 | Ryu et al. |
| 2005/0239115 | A1 | 10/2005 | Ryu et al. |
| 2005/0286576 | A1 | 12/2005 | Gill et al. |
| 2006/0012784 | A1 | 1/2006 | Ulmer |
| 2006/0012793 | A1 | 1/2006 | Harris |
| 2006/0024711 | A1 | 2/2006 | Lapidus et al. |
| 2006/0051876 | A1 | 3/2006 | Bridgham et al. |
| 2006/0146334 | A1 | 7/2006 | Cluff et al. |
| 2006/0263777 | A1 | 11/2006 | Tong |
| 2006/0274408 | A1 | 12/2006 | Lauer |
| 2007/0031875 | A1 | 2/2007 | Buzby |
| 2007/0070349 | A1 | 3/2007 | Harris et al. |
| 2007/0082562 | A1 | 4/2007 | Van Der Lee et al. |
| 2007/0087362 | A1 | 4/2007 | Church et al. |
| 2007/0099208 | A1 | 5/2007 | Drmanac et al. |
| 2007/0231825 | A1 | 10/2007 | Banerjee et al. |
| 2007/0273863 | A1 | 11/2007 | Leep et al. |
| 2008/0140341 | A1 * | 6/2008 | Ralston et al. ............. 702/155 |
| 2008/0176145 | A1 | 7/2008 | Ohnuma |
| 2008/0241936 | A1 | 10/2008 | Banerjee et al. |
| 2008/0315095 | A1 | 12/2008 | Nakasuji et al. |
| 2009/0061505 | A1 * | 3/2009 | Hong et al. ............. 435/287.2 |
| 2009/0061526 | A1 | 3/2009 | Hong et al. |

OTHER PUBLICATIONS

Title:Resolution Improvement in OpticalMicroscopy by Use of Multi-Beam Interferometric Illumination Author: Jekwan Ryu Date: Sep. 2003.*

Cragg, G. et al., "Lateral Resolution Enhancement with Standing Evanescent Waves," Optics Letters, Jan. 1, 2000, vol. 25, No. 1, pp. 46-48.

Freimann, R., et al., "Development of a standing-wave fluorescence microscope with high nodal plane flatness," Journal of Microscopy, Sep. 1997, pp. 193-200, vol. 187, Pt. 3.

Frohn, J., et al., "True optical resolution beyond the Rayleigh limit achieved by standing wave illumination," PNAS, Jun. 20, 2000, pp. 7232-7236, vol. 97, No. 13.

Frohn, J., et al., "Three-dimensional resolution enhancement in fluorescence microscopy by harmonic excitation," Optic Letters, Jun. 1, 2001, pp. 828-830, vol. 26, No. 11.

Gustafsson, M.G.L., "Surpassing the lateral resolution limit by a factor of two using structured illumination microscopy," Journal of Microscopy, May 2000, pp. 82-87, vol. 198, Pt. 2.

Hong, S., et al., "Lensless focusing with subwavelength resolution by direct synthesis of the angular spectrum," Applied Physics Letters, Jun. 29, 2006, vol. 88, pp. 261107-1-261107-3.

Kim, J., et al., "Polony Multiplex Analysis of Gene Expression (PMAGE) in Mouse Hypertrophic Cardiomyopathy," Science, Jun. 8, 2007, pp. 1481-1484, vol. 316, with Supporting Online Material downloaded from the Internet at http://www.sciencemag.org/cgi/data/316/5830/1481/DC1/2 attached.

Ryu, J., et al., "Multibeam interferometric illumination as the primary source of resolution in optical microscopy," Applied Physics Letters, Apr. 28, 2006, vol. 88, pp. 171112-1-171112-3.

Ryu, J., "Resolution Improvement in Optical Microscopy by Use of Multi-Beam Interferometric Illumination," Ph.D. Dissertation, Massachusetts Institute of Technology, 2003, pp. 3, 7-9, 109-111, and 119-122.

Shendure, J., et al., "Accurate Multiplex Polony Sequencing of an Evolved Bacterial Genome," Science, Sep. 9, 2005, pp. 1728-1732, vol. 309, with Supporting Online Material downloaded from the Internet at http://www.sciencemag.org/cgi/data/1117389/DC1/1 attached.

Korean Intellectual Property Office, Office Action, Korean Patent Application No. 10-2010-7004824, Jun. 5, 2012, twelve pages.

PCT International Search Report and Written Opinion, PCT Application No. PCT/US2011/028792, May 26, 2011, seven pages.

PCT International Search Report and Written Opinion, PCT Application No. PCT/US2011/028796, May 13, 2011, eight pages.

Korean Intellectual Property Office, Office Action, Korean Patent Application No. 10-2010-7004824, Oct. 21, 2011, eleven pages.

Zhi, Z. et al., "Microfabrication of Encoded Microparticle Array for Multiplexed DNA Hybridization Detection," Chem. Commun., 2005, pp. 2448-2450.

Ryu, J., "Resolution Improvement in Optical Microscopy by Use of Multi-Beam Interferometric Illumination," Ph.D. Dissertation, Massachusetts Institute of Technology, Sep. 2003, 122 pages.

Chinese State Intellectual Property Office, First Office Action, Chinese Application No. 200880104704.6, Dec. 19, 2011, seventeen pages.

Taiwan Republic of China Intellectual Property Office, Search Report, Taiwan Patent Application No. 097131816, Dec. 18, 2012, eight pages.

* cited by examiner

SYNTHETIC APERTURE OPTICS IMAGING METHOD USING MINIMUM SELECTIVE EXCITATION PATTERNS

CROSS-REFERENCE TO RELATED APPLICATION

This application is related to U.S. patent application Ser. No. 12/728,140, filed concurrently herewith, entitled "Illumination Apparatus Optimized for Synthetic Aperture Optics Imaging Using Minimum Selective Excitation Patterns."

BACKGROUND OF THE INVENTION

1. Field of the Invention

The present invention relates generally to the field of optical microscopy imaging which uses structured or selective illumination or excitation and, more specifically, to a method using a minimum number of selective excitation patterns optimized for imaging of DNA microparticles.

2. Description of the Related Art

Synthetic Aperture Optics (SAO) imaging refers to an optical imaging method in which a series of patterned or structured light patterns are used to illuminate the imaging target in order to achieve resolution beyond what is set by physical constraints of the imaging apparatus such as the lens and the camera. In SAO, an imaging target is selectively excited in order to detect the spatial frequency information of the target. Since there is a one-to-one relationship between the frequency (or Fourier) domain and the object (or target) domain, SAO can reconstruct the original imaging target by obtaining its spatial frequency information.

FIG. 1A illustrates a conventional SAO method, and FIG. 1B illustrates a conventional SAO system. Referring to FIGS. 1A and 1B together, in conventional SAO, selective excitation (or illumination) 104 is applied to an imaging target 102, and the light scattered or fluoresced from the imaging target 102 is captured by optical imaging 106. The imaging target 102 can be composed of micro-particles in a randomly or regularly distributed pattern. Selective excitation (or illumination) 104 may be applied to the imaging target 102 by an illumination apparatus (not shown in FIGS. 1A and 1B) that is configured to cause interference 122 of two or more light beams 131, 132 on the imaging target 102. The excitation is selective or patterned, unlike uniform illumination used in conventional optical imaging techniques. For example, two beams 131, 132 may overlay or interfere on an imaging-target plane 102 to produce a two-dimensional (2D) sinusoidal excitation pattern.

FIG. 1C illustrates an example of a selective excitation pattern in the spatial domain and the frequency domain. Referring to FIGS. 1B and 1C, the exemplary selective excitation pattern 140 in the spatial domain is generated by interference of two beams 131, 132 on the imaging-target plane 102, resulting in a 2D sinusoidal excitation pattern. The angle ($\phi$) between the two beams 131, 132 determines the pitch 143 of the pattern, which represents the spacing or periodicity of 2D sinusoidal fringe pattern 140. More specifically, the pitch 143 is substantially inversely proportional to $\sin(\phi)$. The orientation $\phi$ of the pattern represents the amount of angular rotation of the 2D sinusoidal fringes 140 compared to its reference pattern, which in this example of FIG. 1C is shown as a 2D sinusoid comprised of vertical lines, although a different reference pattern such as a 2D sinusoid comprised of horizontal lines can also be used as the reference pattern. In mathematical terms, the orientation $\phi$ can be described as follows: if u is the normal vector of the plane formed by the two beams 131, 132 and if the projected vector of u on the imaging plane 102 is called v, then the orientation $\phi$ of the sinusoidal pattern 140 is the angular orientation of the vector v with respect to the frame of reference. The "phase" of the pattern is the periodic position of the 2D sinusoid with respect to the frame of reference. The range of the phases of the 2D sinusoid excitation pattern will be a value between 0 and $2\pi$. The different phases can be obtained by changing optical path length of one beam.

As shown in FIG. 1C, the 2D sinusoid excitation pattern in the spatial domain can be shown as a conjugate pair $k_i$, $k_i'$ in the corresponding frequency domain (k-space). Each conjugate pair in the k-space corresponds to the pitch 143 and orientation $\phi$ of the corresponding 2D sinusoid pattern. The pitch 143 of the 2D sinusoid pattern 140 is determined by the radial distance r of the k-space point—more precisely, the pitch 143 is substantially the inverse of the radial distance r in the frequency domain. The orientation $\phi$ is the angle $\phi$ of the k-space points in a radial coordinate system in the frequency domain. Thus, a number of different excitation patterns may be generated by changing the pitch 143 of the 2D sinusoid pattern (or the angle ($\phi$) between the two beams 131, 132) and changing the orientation $\phi$ of the 2D sinusoid pattern, with each different pair of pitch 143 and orientation $\phi$ of the 2D sinusoid pattern in the spatial domain corresponding to a different conjugate pair (radial distance r and orientation $\phi$) in the k-space (frequency) domain.

Referring back to FIGS. 1A and 1B, the excited target 102 emits signals (or photons), and the signals are captured in optical imaging system 106 including an objective lens 124 and an imaging sensor (or imager) 126. The emitted signal will have a wavelength $\lambda_E$. The objective lens has magnification (Mag) and a numerical aperture $NA = n \times \sin \theta$, where n is the index of refraction of the medium in which the lens 124 is placed and $\theta$ is the half-angle of the maximum cone of light that can enter or exit the lens 124. Typically, the imaging sensor 126 can be a charge-coupled device (CCD), complementary metal-oxide-semiconductor (CMOS) image sensor, or any other photon detectors in a matrix or array format including a plurality of pixels m. Note that, in some applications, the emitted signals from the target 102 may be directly captured by the imager 126 without going through the objective lens 124.

Then, it is determined 108 whether the images corresponding to all the phases of the 2D sinusoid excitation pattern were obtained. If images corresponding to all the phases of the 2D sinusoid excitation pattern were not obtained in step 108, the excitation phase is changed 114 and steps 104, 106, 108 are repeated for the changed excitation phase. If images corresponding to all the phases of the 2D sinusoid excitation pattern were obtained in step 108, then it is determined 110 whether the images corresponding to all the 2D sinusoid selective excitation patterns were obtained. If images corresponding to all the 2D sinusoid selective excitation patterns were not obtained in step 110, the excitation pattern is changed by using a different spatial frequency (e.g., changing the pitch 143 and the orientation $\phi$ of the 2D sinusoid pattern) and steps 104, 106, 108, 114 are repeated for the next selective excitation pattern.

If images corresponding to all the 2D sinusoid selective excitation patterns were obtained in step 110, then finally the captured images are sent to a computer for SAO post processing 112 and visualization. In conventional imaging, the resolution of the SAO imaging system is determined by the numerical aperture NA of the lens 124, the wavelength $\lambda_E$ of the emitted light, and the pixel size. In contrast, in SAO imaging, the resolution of the imaging system is beyond what can be achieved by the numerical aperture NA of the lens 124, the wavelength $\lambda_E$ of the emitted light, and the pixel size. Thus, as shown in FIG. 1B, the images captured through steps 104, 106, 108 of FIG. 1A are raw images $RI_i$, with a resolution lower than (insufficient for) the resolution needed to resolve the objects on the imaging target 102. However, multiple sets of the lower resolution raw images RI, are captured for different excitation phases and spatial frequencies (excitation patterns) to obtain the complete raw image set 128, which then goes through SAO post-processing 112 to synthesize the final image FI that has a resolution higher than the resolution of the raw images $RI_i$. The resolution of the final image FI obtained by SAO post-processing is sufficient for resolution of the objects on the imaging target 102. The methodology for SAO post-processing 112 for synthesizing high resolution images FI from lower resolution raw images RI, is well known. Raw images RIi are converted into k-space information of the high resolution images FI, and this information is Fourier transformed to synthesize or reconstruct the high resolution images FI. For example, one example of the SAO post-processing methodology can be found in U.S. Pat. No. 6,016,196, issued on Jan. 18, 2000 to Mermelstein, entitled "Multiple Beam Pair Optical Imaging," which is incorporated by reference herein.

Applying SAO to DNA (deoxyribonucleic acid) or RNA (ribonucleic acid) sequencing presents a number of challenges. The term "nucleic acid" herein includes both DNA and RNA. In DNA or RNA sequencing, single molecule or amplified clones of a DNA template (collectively referred to as "microparticle") are immobilized onto a planar substrate. The array of microparticles then goes through multiple cycles of chemical reaction and optical detection. FIGS. 2A, 2B, and 2C illustrate different types of individual sequencing microparticles that can be used for DNA sequencing. FIG. 2A illustrates an individual microparticle 202 formed by a 1-micrometer diameter bead 208 covered with clonal DNA molecules 210 that have been previously amplified by a water-in-oil emulsion PCR technique. The bead 208 is attached directly to the substrate 204 in fluid 206. FIG. 2B illustrates an individual microparticle 202 as a cluster of clonal DNA molecules 210 attached to the substrate 204 and placed in fluid 206. The DNA molecules 210 have been previously amplified by a bridge amplification technique. FIG. 2C illustrates an individual microparticle as a single DNA molecule 210 attached to the substrate 204 and placed in fluid 206. The single DNA molecule 210 is sequenced without amplification.

The distribution of DNA microparticles can be random or regular. FIGS. 3A and 3B illustrate some examples of the distribution of DNA microparticles. If Δx is defined to be the spatial resolution of an imaging system (i.e., Δx is the minimum distance of two point objects that can be resolved by the imaging system), Δx is typically designed to be about half of the distance between adjacent microparticles 202 (see FIG. 3A). In DNA sequencing applications, it is highly desirable for an optical imaging system to achieve both high resolution and high scanning speed at the same time. SAO imaging is promising since it can image a large area using a low magnification lens and camera without sacrificing resolution. The resolution of SAO imaging is obtained from the high resolution illumination patterns and post-processing. However, SAO requires selective excitation to be repeated for a number of selective excitation patterns. Conventional SAO imaging uses a large number of SAO excitation patterns, often including many redundant or even irrelevant illumination patterns. The number of excitation patterns in conventional SAO is merely determined based on the hardware architecture of the illumination system, without regard to other factors. The large number of excitation patterns in conventional SAO makes it impractical for use in DNA sequencing, as conventional SAO does not offer the cost and throughput benefit in DNA sequencing compared to conventional optics. Also, conventional SAO hardware is large, complex, difficult to scale, and mechanically and thermally unstable, requiring large space and extremely careful control of temperature and mechanical vibration for continuous run, making it particularly impractical for use in DNA sequencing which requires repeated, continuous runs of SAO over a very large number of DNA microparticle arrays.

SUMMARY OF THE INVENTION

Embodiments of the present invention include a method for synthetic aperture optics (SAO) that minimizes the number of selective excitation patterns used to illuminate the imaging target based on the target's physical characteristics corresponding to spatial frequency content from the illuminated target and/or one or more parameters of the optical imaging system used for SAO. Embodiments of the present invention also include an SAO apparatus that includes a plurality of interference pattern generation modules that are arranged in a half-ring shape.

In one embodiment, an SAO method comprises illuminating the target including one or more objects with a predetermined number (N) of selective excitation patterns, where the number (N) of selective excitation patterns is determined based upon the objects' physical characteristics corresponding to spatial frequency content from the illuminated target, optically imaging the illuminated target at a resolution insufficient to resolve the objects on the target, and processing optical images of the illuminated target using information on the selective excitation patterns to obtain a final image of the illuminated target at a resolution sufficient to resolve the objects on the target. In another embodiment, the number (N) of selective excitation patterns corresponds to the number of k-space sampling points in a k-space sampling space in a frequency domain, with the extent of the k-space sampling space being substantially proportional to an inverse of a minimum distance (Δx) between the objects that is to be resolved by SAO, and with the inverse of the k-space sampling interval between the k-space sampling points being less than a width (w) of a detected area captured by a pixel of a system for said optical imaging.

In another embodiment, an SAO apparatus comprises a plurality of interference pattern generation modules (IPGMs), with each IPGM configured to generate a pair of light beams that interfere to generate a selective excitation pattern on the target at a predetermined orientation and a predetermined pitch, and with the IPGMs arranged in a half-ring shape. The SAO apparatus also comprises an optical imaging module configured to optically image the illuminated target at a resolution insufficient to resolve the objects on the target. The optical image of the illuminated target is further processed using information on the selective excitation patterns to obtain a final image of the illuminated target at a resolution sufficient to resolve the target. The number of IPGMs is equal to the number of selective excitation patterns used for performing SAO on the target. The IPGMs may be placed substantially symmetrically on a monolithic structure that has the half-ring shape.

According to various embodiments of the present invention, an optimized, minimum number of excitation patterns are used in SAO, thereby enabling SAO to be used with applications such as DNA sequencing that requires massive parallelization of SAO imaging in a short amount of time to make DNA sequencing with SAO commercially feasible. Thus, dramatic increase of throughput and reduction of cost for DNA sequencing can be achieved by using SAO according to the present invention.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

BRIEF DESCRIPTION OF THE DRAWINGS

The teachings of the embodiments of the present invention can be readily understood by considering the following detailed description in conjunction with the accompanying drawings.

Figure (FIG.) 1A illustrates a conventional SAO method.

DETAILED DESCRIPTION OF EMBODIMENTS

The Figures (FIG.) and the following description relate to preferred embodiments of the present invention by way of illustration only. It should be noted that from the following discussion, alternative embodiments of the structures and methods disclosed herein will be readily recognized as viable alternatives that may be employed without departing from the principles of the claimed invention.

Reference will now be made in detail to several embodiments of the present invention(s), examples of which are illustrated in the accompanying figures. It is noted that wherever practicable similar or like reference numbers may be used in the figures and may indicate similar or like functionality. The figures depict embodiments of the present invention for purposes of illustration only. One skilled in the art will readily recognize from the following description that alternative embodiments of the structures and methods illustrated herein may be employed without departing from the principles of the invention described herein.

Synthetic aperture optics (SAO) imaging method according to various embodiments of the present invention minimizes the number of selective excitation patterns used to illuminate the imaging target, based on the target's physical characteristics corresponding to spatial frequency content from the illuminated target and/or one or more parameters of the optical imaging system used for SAO. Embodiments of the present invention also include an SAO apparatus that is optimized to perform the SAO method according to the present invention. The SAO apparatus includes a plurality of interference pattern generation modules that are arranged in a half-ring shape, each of which generates one selective excitation pattern for SAO.

Figure 1A:
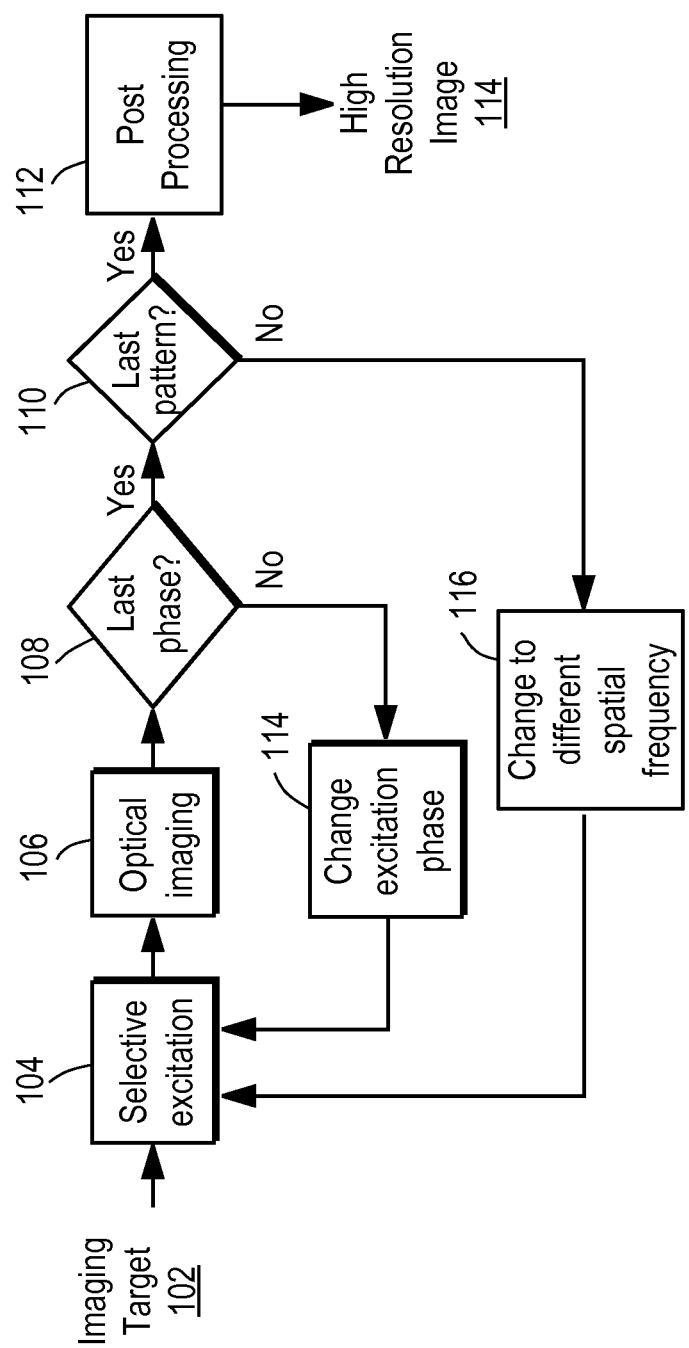
FIG. 1B illustrates a conventional SAO system.
FIG. 1C illustrates an example of a selective excitation pattern in the spatial domain and the frequency domain.
Figure 1B:
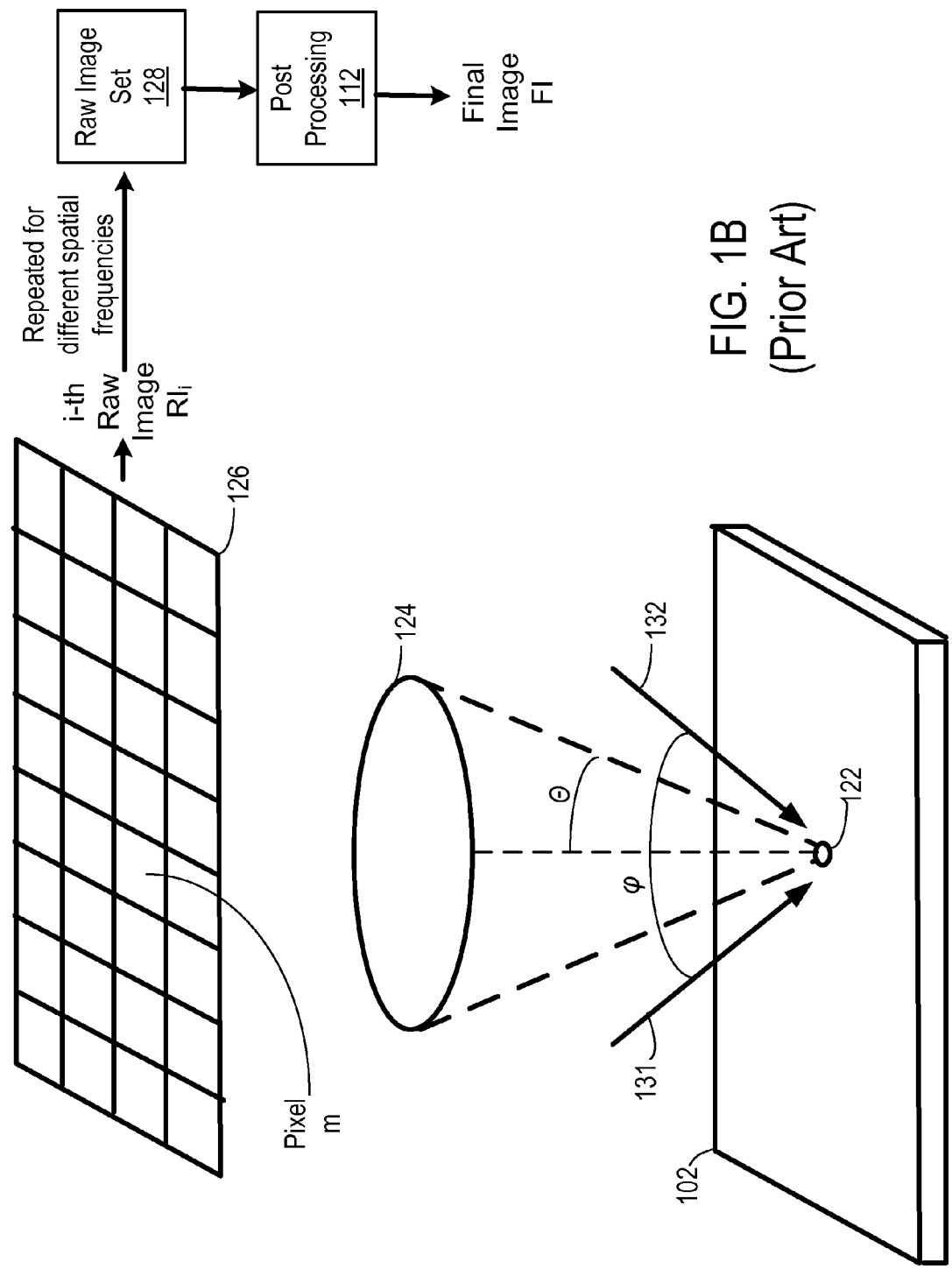
Figure 1C:
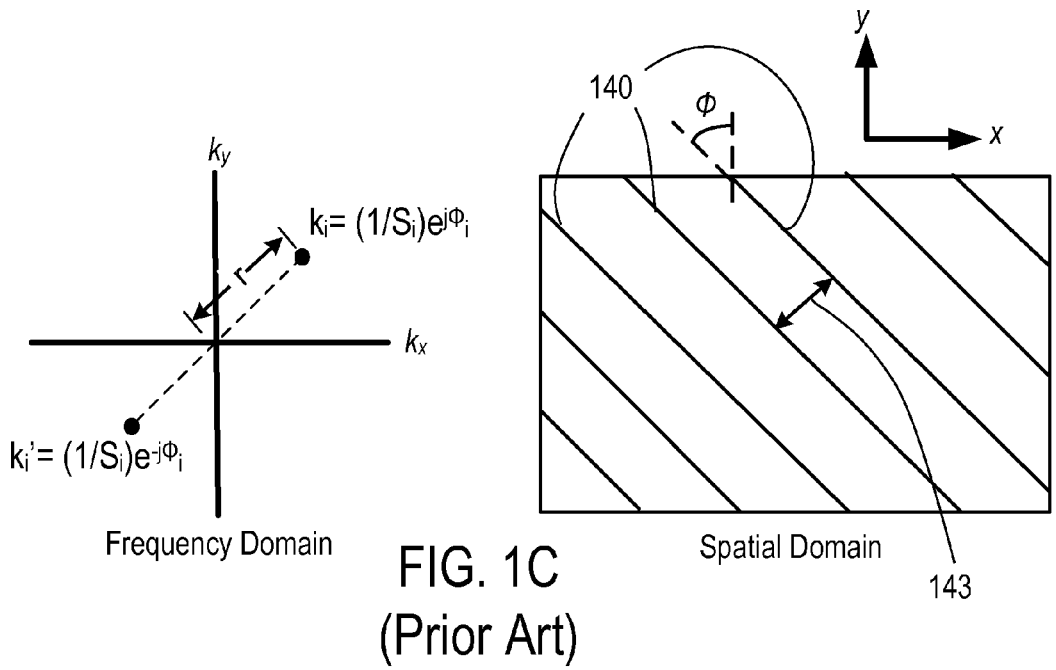
Figure 2A:
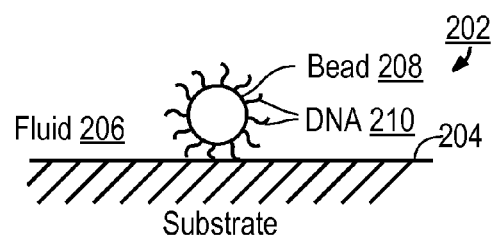
FIGS. 2A, 2B, and 2C illustrate different types of individual sequencing microparticles that can be used for DNA sequencing.
Figure 2B:
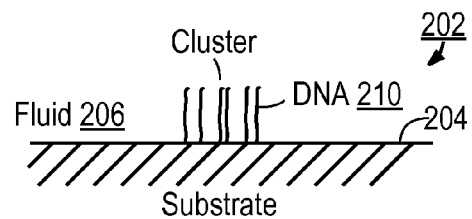
Figure 2C:
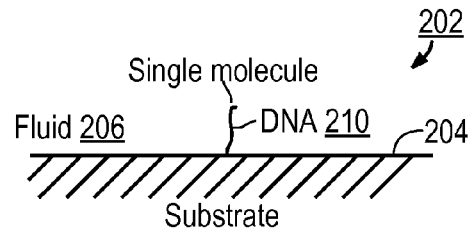
Figure 3B:
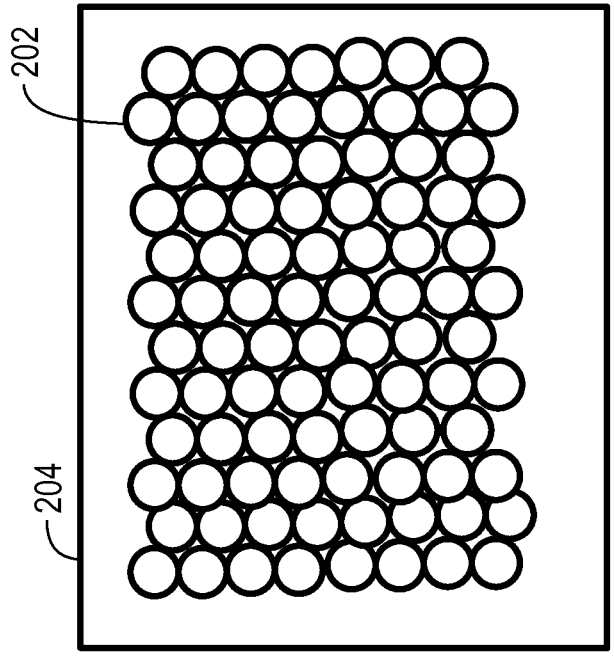
FIGS. 3A and 3B illustrate some examples of the distribution of DNA microparticles.
Figure 3A:
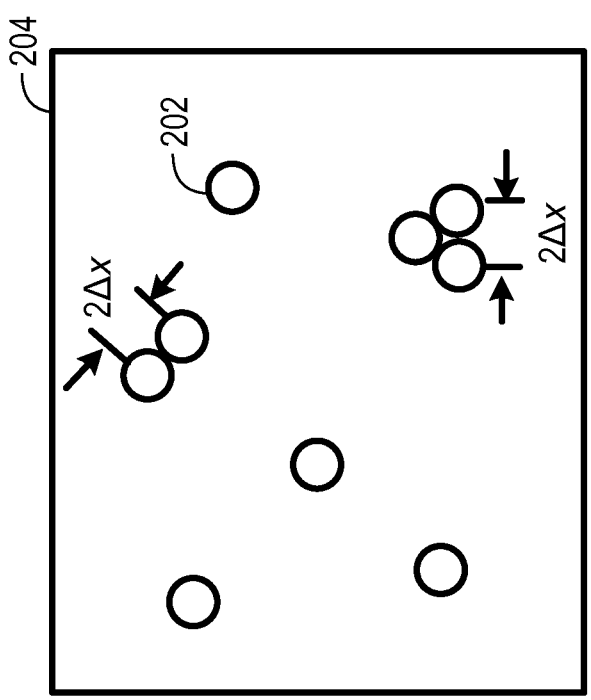
Figure 4:
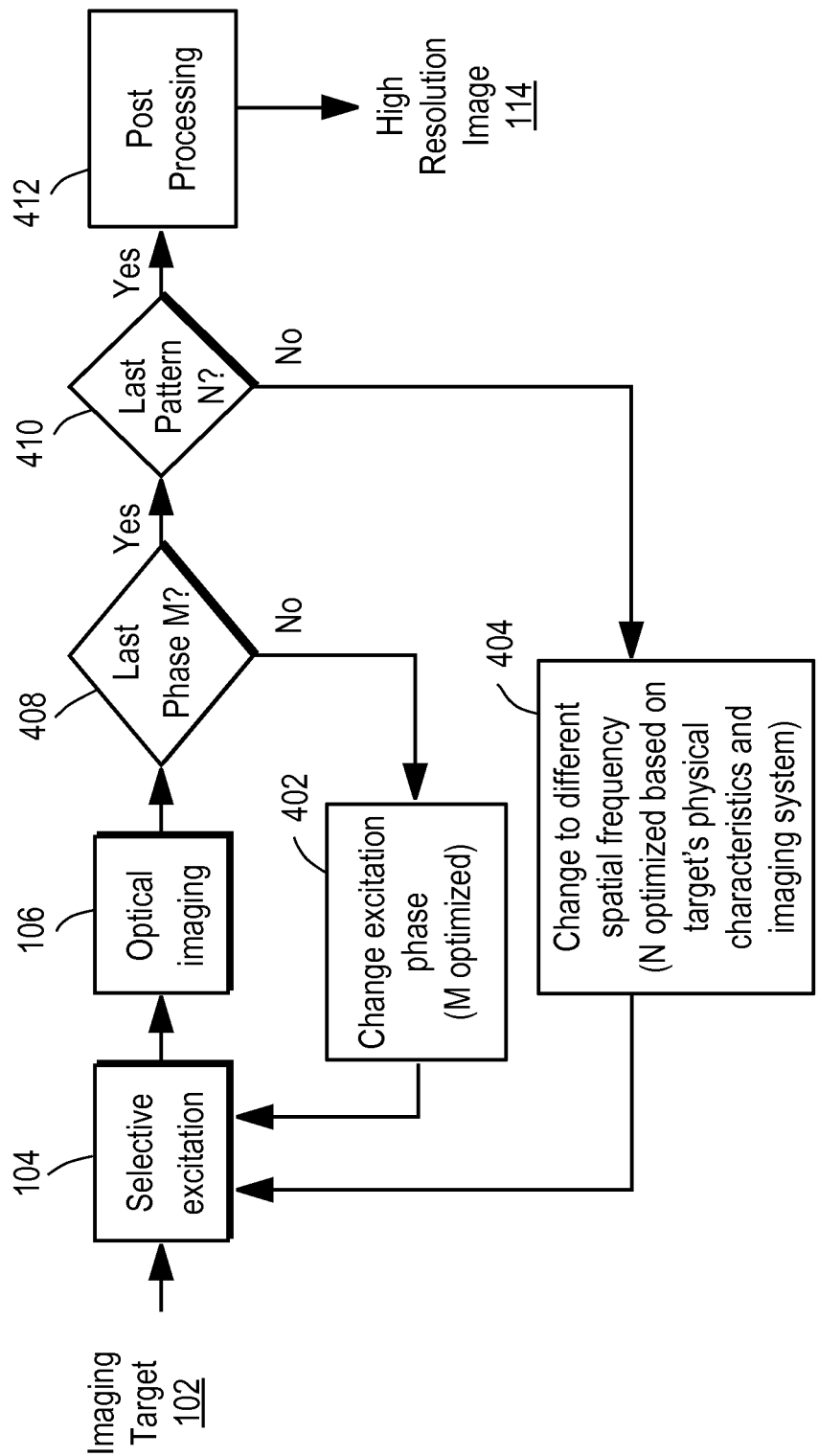
FIG. 4 illustrates an SAO method, according to one embodiment.

Turning to the figures, FIG. 4 illustrates an SAO method, according to one embodiment. As is typical with SAO imaging, selective excitation (or illumination) 104 is applied to an imaging target 102, and the light scattered or fluoresced from the imaging target 102 is captured by optical imaging 106. Here, the imaging target 102 is assumed to be a DNA microparticle such as those illustrated in FIGS. 2A-2C, 3A, and 3B. As will be explained in more detail below with reference to FIGS. 7A-7D, selective excitation 104 is applied to the imaging target 102 by an illumination apparatus that is configured to cause interference of two light beams on the imaging target 102. The excited target 102 emits signals (or photons), and the emitted signals are captured in an optical imaging system 106 including an objective lens and an imaging sensor (or imager). Then, it is determined 408 whether the images corresponding to all M phases of the 2D sinusoid excitation pattern were obtained. If images corresponding to all the phases of the 2D sinusoid excitation pattern were not obtained in step 408, the excitation phase is changed 402 and steps 104, 106, 408 are repeated for the changed excitation phase. If images corresponding to all the phases of the 2D sinusoid excitation pattern were obtained in step 408, then it is determined 410 whether the images corresponding to all the 2D sinusoid selective excitation patterns were obtained. If images corresponding to all the 2D sinusoid excitation patterns were not obtained in step 410, the excitation pattern is changed by using a different spatial frequency (e.g., changing the pitch 143 and the orientation φ of the 2D sinusoid pattern) and steps 104, 106, 408, 402, 410, 404 are repeated for the next selective excitation pattern. Then, if images corresponding to all the 2D sinusoid excitation patterns were obtained in step 410, then the captured images are sent to a computer for SAO post processing 412 and visualization to obtain the high-resolution images 114 of the imaging target 102 from the captured lower resolution raw images. As explained above, the raw images captured by optical imaging 106 have a resolution insufficient to resolve the objects on the imaging target 102, while the high resolution image 114 reconstructed by SAO post-processing 412 have a resolution sufficient to resolve the objects on the imaging target 102.

The SAO method of the present invention uses an optimized number N of selective excitation patterns and an optimized number M of excitation phases of each selective excitation pattern, so that SAO can be used to image targets such as DNA microparticles in a massively parallel manner within a short amount of time. As explained above, the number of selective excitation patterns used in conventional SAO is determined merely by the hardware characteristics of the illumination system, independent and without consideration of the imaging target or the imaging system (objective lens and camera). Thus, the number of k-space sampling points corresponding to the selective excitation patterns in conventional SAO was not optimized, and has many redundant and sometimes irrelevant k-space sampling points. In contrast, SAO according to the embodiments of the present invention herein uses selective excitation patterns whose number N is optimized and minimized as a function of the imaging target's physical characteristics corresponding to spatial frequency content (e.g., the size, shape, and/or spacing of the objects on the imaging target). SAO according to the embodiments herein may also use selective excitation patterns whose number N is optimized alternatively or additionally as a function of various parameters of the imaging system (e.g., magnification (Mag) of the objective lens, numerical aperture (NA) of the objective lens, wavelength $\lambda_E$ of the light emitted from the imaging target, and/or effective pixel size p of the pixel sensitive area of the CCD, etc.). In this manner, the resulting number N of excitation patterns used in SAO becomes much smaller than that in conventional SAO, thereby enabling SAO to be used with DNA sequencing that requires massive parallelization of SAO imaging in a short amount of time to make DNA sequencing commercially feasible. Thus, dramatic reduction of cost and increase of throughput of DNA sequencing can be achieved.

Figure 5A:
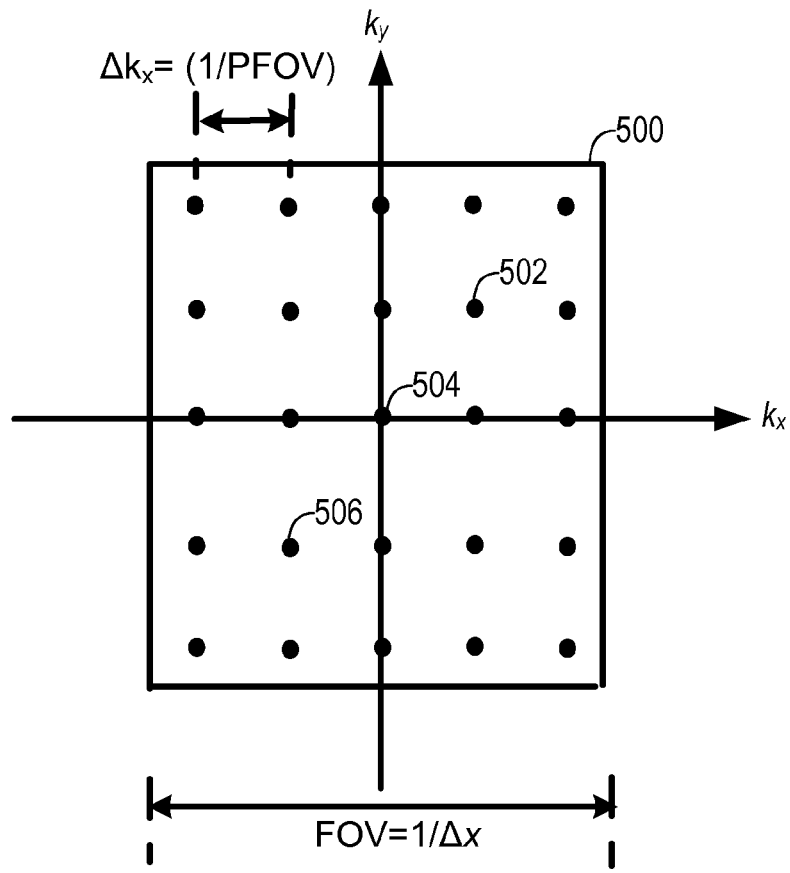
FIG. 5A illustrates the k-space sampling points (selective excitation patterns) used in SAO, according to one embodiment.

FIG. 5A illustrates the k-space sampling points (selective excitation patterns) used in SAO, according to one embodiment. In FIG. 5A, it is assumed that the CCD imaging area has a square shape and thus a square shaped k-space sampling space 500 for SAO is also assumed, although the description for FIG. 5A below can be applied to a non-square shaped (e.g., rectangular) k-space sampling space as well. The k-space sampling space 500 has an area of $FOV^2$, with the extent of the k-space sampling space in each of the horizontal and vertical directions being FOV. Here, FOV stands for the k-space field of view. In the k-space frequency domain, FOV should be equal to $(1/\Delta x)$, where $\Delta x$ the spatial resolution of an imaging system (i.e., $\Delta x$ is the minimum distance of two point objects that can be resolved by the imaging system). Each conjugate pair 502, 506 and its DC point 504 correspond to one selective excitation pattern for SAO as used with the present invention. Thus, the number of selective excitation patterns used in SAO corresponds to the number of conjugate pairs of k-space points in the k-space sampling space 500 (FOV x FOV). $\Delta k_x$ is the k-space sampling interval, and is equal to (1/PFOV) where PFOV is the pixel field of view. The smaller the k-space sampling interval $\Delta k_x$ is in the k-space sampling space 500, the larger the number of k-space points and the corresponding number of excitation patterns are. Specifically, the following equations hold:

$$N = \text{floor}(L/2) \quad \text{(Equation 1)},$$

where L is the number of k-space points in the k-space, N is the number of selective excitation patterns, and floor ( ) rounds the number to the nearest but smallest integer;

$$L = \text{round}((FOV/\Delta k_x)^2) = \text{round}((PFOV/\Delta x)^2) \quad \text{(Equation 2)},$$

where round ( ) rounds the number to the nearest integer, and PFOV is the extent in the reciprocal (or Fourier) space of the sampling space (k-space) to be reconstructed from the samples.

Figure 5B:
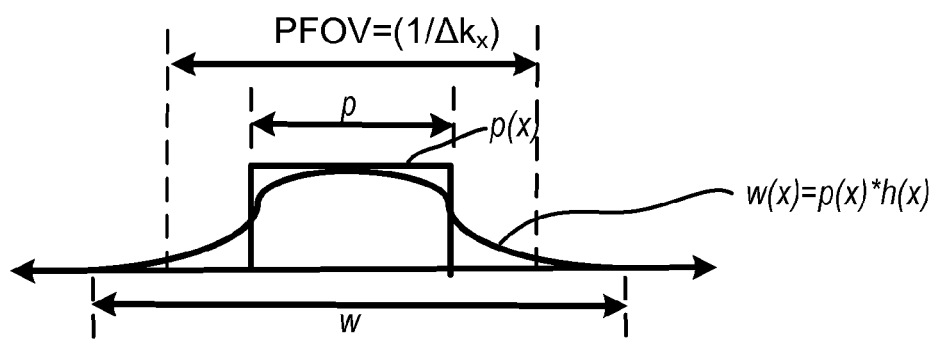
FIG. 5B illustrates the selection of the k-space sampling interval used in SAO, according to one embodiment.

FIG. 5B illustrates the selection of the k-space sampling interval used in SAO, according to one embodiment. As explained above, the imaging target size determines the required spatial resolution $\Delta x$. Magnification (Mag) and CCD pixel size (Z) determines the effective pixel size p on the imaging-target plane, p=Z/Mag. As shown in FIG. 5B, the detected area w(x) (i.e., the area captured by the pixel) can be represented as the convolution of the pixel-sensitivity function p(x) (e.g., the rectangular function with width p) and the point-spread function (PSF) h(x) of the lens (e.g., a bell-shaped curve). The width w can be defined as the $1/e^2$ width of detected area w(x). Since the PSF of the lens is determined by the NA of the lens, the extent of the detected area (w) and the weighting over the detected area (i.e., the effective sensitivity profile over the detected area) are the function of the magnification (Mag) of the lens, numerical aperture (NA) of the lens, and the CCD pixel size (Z).

As can be seen from the above, the k-space sampling space (FOV) is determined by the desired spatial resolution $\Delta x$ and is dictated by the imaging target. DNA microparticles typically have a very small size, resulting in a large k-space sampling space. In conventional SAO, the k-space sampling interval $\Delta k_x$ is set without regard to the physical characteristics of the imaging target or the parameters of the imaging system, and is rather just set randomly according to whatever interval allowed by the SAO illumination system. This made the number of k-space points and the resulting selective excitation patterns prohibitively large for use in DNA sequencing applications using SAO, because of the high cost and low throughput of DNA sequencing using such large number of selective excitation patterns in SAO.

In contrast, SAO according to the embodiments of the present invention herein use selective excitation patterns whose number N is optimized as a function of the imaging target's physical characteristics corresponding to spatial frequency content (e.g., the size, shape, and/or spacing of the imaging target). As shown in FIG. 5B, in one embodiment, the pixel field of view PFOV is selected to be smaller than the extent (w) of the detected area, i.e., PFOV<w. Using a small PFOV results in a larger k-space sampling interval $\Delta k_x$, thereby reducing the number (L) of k-space points in the k-space sampling space 500 and the resulting number (N) of selective excitation patterns for use in SAO. As will be explained in more detail below with reference to FIGS. 6A and 6B, using PFOV smaller than the extent (w) of the detected area causes aliasing in the high resolution image obtained from SAO, but such aliasing can be removed using the method as described below with reference to FIG. 6C. In other embodiments, the PFOV may be set to be equal to or larger than the extent (w) of the detected area, thereby preventing aliasing from occurring in the high resolution image obtained from SAO. Also note that setting PFOV with consideration of the extent (w) of the detected area effectively sets the k-space sampling interval ($\Delta k_x$) and the resulting number (N) of selective excitation patterns based on the various parameters of the imaging system, since the extent (w) of the detected area is a function of the magnification (Mag) of the lens, numerical aperture (NA) of the lens, and the CCD pixel size (Z) as explained above.

Furthermore, SAO according to the embodiments herein further reduces the number of iterations of selective excitation and imaging by minimizing the number of phase changes (M in steps 402, 408 of FIG. 4). Referring back to FIG. 5A and as explained above, one conjugate pair 502, 506 of k-space points corresponds to one SAO interference pattern generation module that produces a specific pitch and orientation of one selective excitation pattern. The DC point 504 corresponds to the signal offset of the 2D sinusoid selective excitation pattern. Thus, in one embodiment, three different measurements at three different phases of the interference pattern with the same pitch and orientation are made to distinguish between the two conjugate points 502, 506 and the DC point 504 in the k-space. This is in contrast to conventional SAO, where more than three phases were used to illuminate and image each selective excitation pattern for SAO. In another embodiment, since the DC point 504 is common for all conjugate pairs 502, 506, it is also possible to utilize the DC point 504 obtained in one 2D sinusoid pattern with a specific pitch and orientation to obviate the need for illuminating and imaging the selective excitation pattern at the DC point 504 of another selective excitation pattern with a different pitch and orientation, thereby reducing the number M of changed phases needed for imaging in steps 402, 408 (FIG. 4) to two (2) phases for the other selective excitation patterns. In other words, each interference pattern generation module produces a pattern with only two different phases, except one module that produces a pattern with three different phases to acquire the DC point 504. For optimal tolerance to noise, one can choose specific phases for the patterns. For three different phases per a specific selective excitation pattern, the optimal phase difference may be 0, 120, and 240 degrees. For two different phases per a specific selective excitation pattern, the optimal phase difference may be 0 and 90 degrees.

Figure 5C:
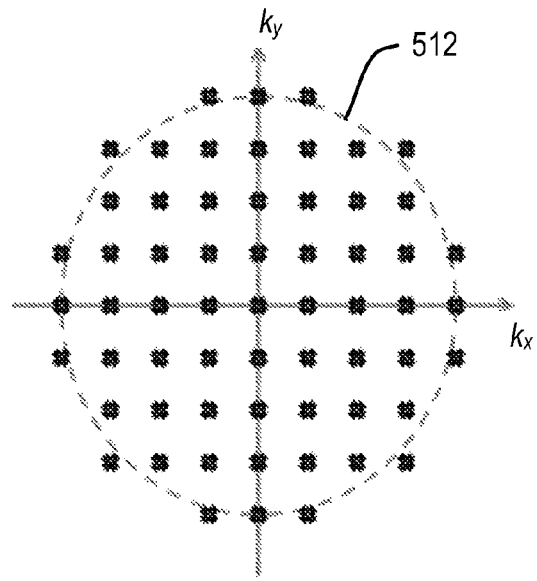
FIG. 5C illustrates using selective excitation patterns corresponding to k-space sampling points within a circular region, according to one embodiment.

Since the objects of interest (i.e., DNA microparticles) are typically circularly symmetric, the k-space spectrum of the objects of interest will also be circularly symmetric and thus only k-space samples in the circular region with diameter of FOV (=1/$\Delta$x) may be needed for SAO. Thus, in one embodiment, the SAO according to the present invention uses selective excitation patterns corresponding to the k-space sampling points within the circular region 512, as shown in FIG. 5C.

Figure 5D:
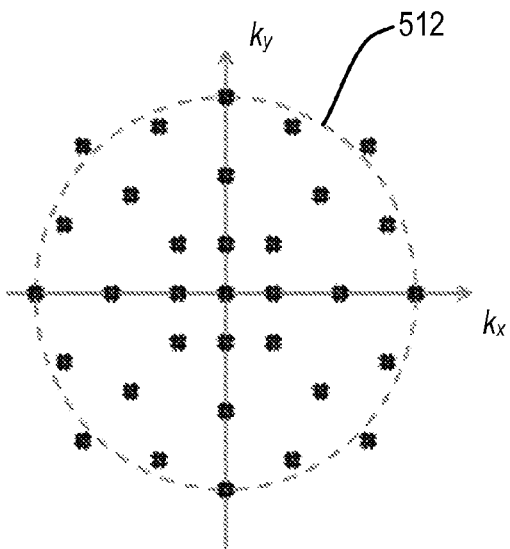
FIG. 5D illustrates reducing the number of k-space sampling points by sparse k-space sampling, according to one embodiment.

FIG. 5D illustrates reducing the number of k-space sampling points by sparse k-space sampling, according to one embodiment. Conventional SAO methods do not utilize frequency information of the objects in the image scene. Solid objects such as beads used in microparticles have much less energy in the high spatial-frequencies compared to the low frequencies. Therefore, under-sampling in the high spatial frequencies is more tolerable than under-sampling in the low spatial frequency region. Thus, in one embodiment of the present invention, the number (N) of selective excitation patterns is further reduced by non-uniform or variable-density sampling in the Fourier space as shown in FIG. 5D. The penalty for not meeting the Nyquist sampling rate in high spatial frequencies is tolerable in SAO for DNA sequencing applications, and thus SAO according to the embodiments herein relaxes the Nyquist sampling criteria in the higher-frequencies, thereby reducing the number of selective excitation patterns by almost half of what would be required with uniform sampling. For example, the number of k-space samples in the embodiment of FIG. 5D is only 54% of the number of k-space samples in the embodiment of FIG. 5C.

Figure 6A:
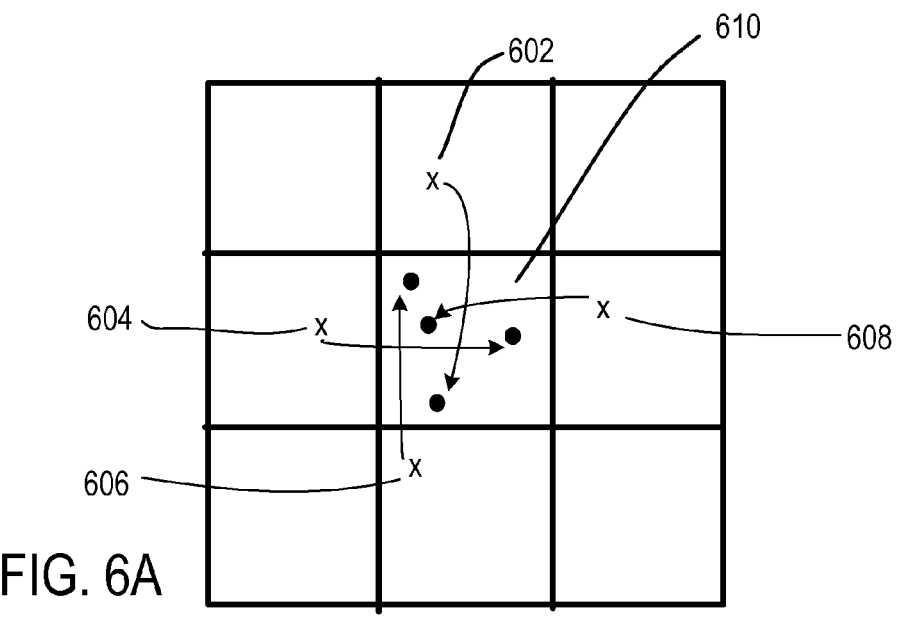
FIG. 6A illustrates how aliasing occurs in SAO by use of a pixel field of view (PFOV) smaller than the detected area, according to one embodiment.

FIG. 6A illustrates how aliasing occurs in SAO by use of a pixel field of view smaller than the detected area, according to one embodiment. As mentioned above with reference to FIG. 5B, using a pixel field of view (PFOV) smaller than the extent (w) of the detected area, i.e., PFOV<w, results in aliasing in the image obtained for SAO, because each pixel in the CCD would detect areas larger than the pixel itself. The extra area (i.e., left and right parts of the extent (w) outside of p(x)) is the area also detected by its neighboring pixels in the CCD. This is illustrated in FIG. 6A, where the objects 602, 604, 606, 608 detected in the extra area in the neighboring pixels will enter into the center pixel 610 (assuming rectilinear sampling in the k-space), resulting in aliasing and unwanted artifacts that degrade the image quality.

Figure 6B:
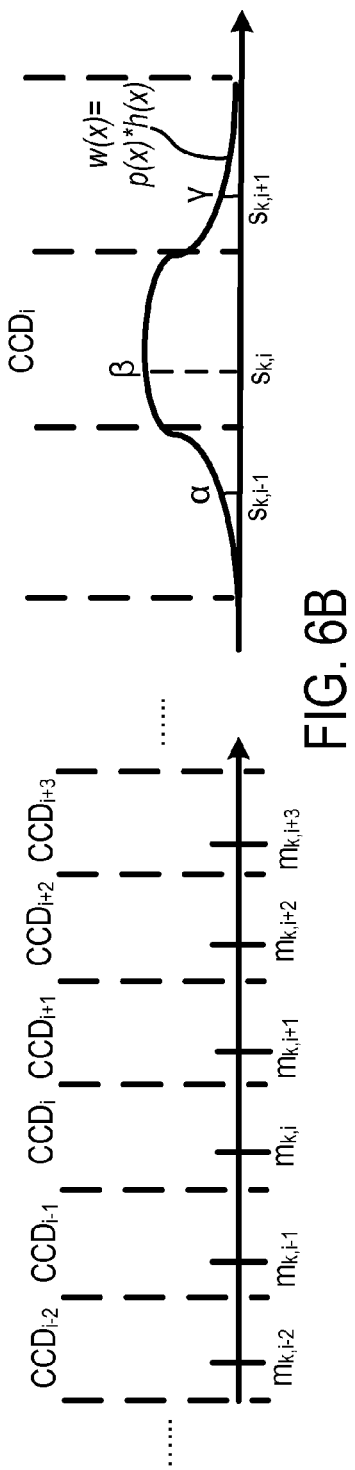
FIG. 6B illustrates how the actual signal at a pixel of an imaging system may be determined by unfolding the measured signal at the pixel to remove aliasing, according to one embodiment.

FIG. 6B illustrates how the actual signal at a pixel of an imaging system may be determined by unfolding the measured signal at the pixel to remove aliasing, according to one embodiment. In order to remove aliasing in the measured image signal and obtain the actual image signals, one can formulate a linear equation in the form of y=Ax at a particular sub-pixel k at pixel $CCD_i$ of the CCD. Referring to FIG. 6B, $m_{k,i}$ represents the measured signal (including aliasing) at a particular k-th sub-pixel location within the i-th CCD pixel $CCD_i$. Note that the relative locations of all measured signals $m_{k,i}$ (i=1, . . . , $\infty$) within their i-th CCD pixels are the same. $s_{k,i}$ represents the actual or ideal signal of the object at the k-th sub-pixel locations within the i-th CCD pixel $CCD_i$. $\alpha$, $\beta$, and $\gamma$ represent the values of the weighting function w(x) of the i-th CCD pixel at the locations corresponding to $s_{k,i-1}$, $s_{k,i}$, and $s_{k,i+1}$, respectively, and $s_{k,i}$ (i=1, . . . , $\infty$) is the actual (ideal) signal at the particular k-th sub-pixel location within the i-th CCD pixel $CCD_i$. As explained above, the weighting function w(x) can be represented as the convolution of the pixel-sensitivity function p(x) (e.g., the rectangular function with width p) and the point-spread function (PSF) h(x) of the lens (e.g., a bell-shaped curve). With these parameters defined and assuming that the number of pixels of the CCD is infinite, one can write the signal-equation series for a particular $k^{th}$ sub-pixel location as a linear matrix equation y=Ax, where y=[$m_{k,1}, m_{k,2}, \ldots$], x=[$s_{k,1}, \ldots s_{k,2}, \ldots$], and A is a matrix with elements being zeros and values of the weighting function (e.g., $\alpha$, $\beta$, and $\gamma$). The linear matrix equation y=Ax shows that the "unfolding" process (i.e., recovering the actual signal $s_{k,i}$) can be viewed as a common inverse problem of y=Ax (i.e., x=$A^{-1}$y). In other embodiments, if non-rectilinear sampling pattern is used (e.g., variable-density, radial sampling, etc.), the actual relationship between $s_i$ and $m_i$ will change from that shown in FIG. 6B, in which case the point-spread-function (i.e., impulse response) can be measured in either simulation or real experiments to construct the inversion matrix ($A^{-1}$).

Figure 6C:
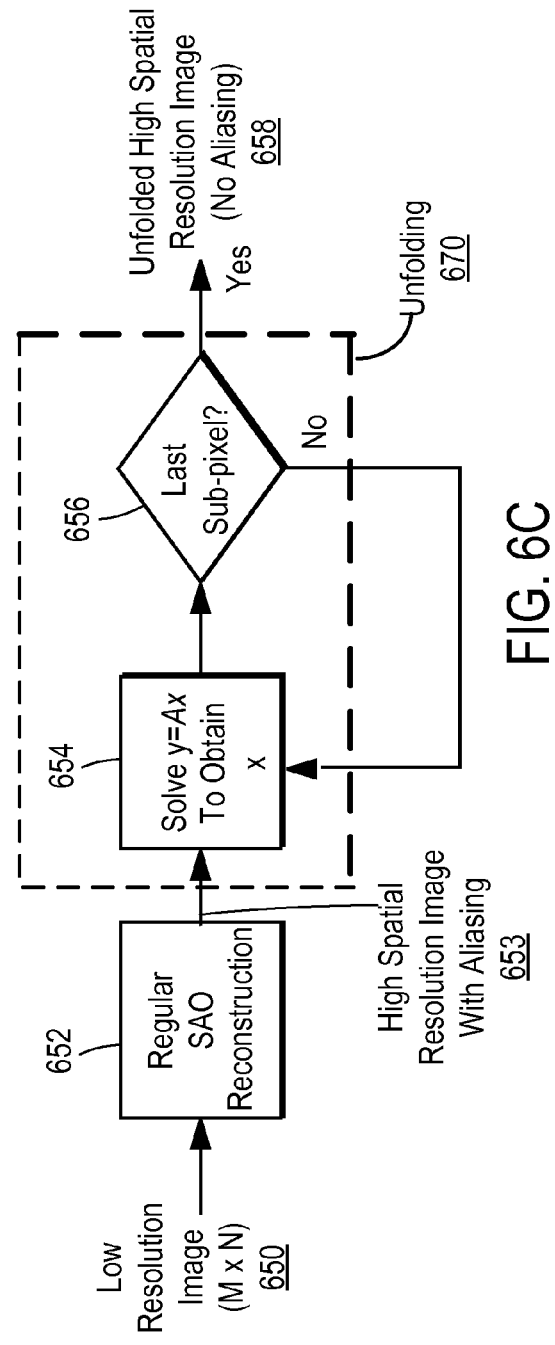
FIG. 6C illustrates a method of unfolding the measured signal at the pixel to remove aliasing, according to one embodiment.

FIG. 6C illustrates a method of unfolding the measured signal at the pixel to remove aliasing, according to one embodiment. The steps 652, 654, 656 together constitute the post-processing steps for SAO. In conventional SAO, post-processing includes only the regular SAO reconstruction 652 to generate the high spatial resolution image 653 from the low resolution images (M×N) 650 obtained from selective excitation of the imaging target. However, in SAO according to the embodiments of the present invention herein, post-processing includes the "unfolding" step 670 to remove aliasing from the high spatial resolution image 653 that contains aliasing resulting from using PFOV smaller than the extent (w) of the detected area for selective excitation. The unfolding process 670 includes solving the linear equation y=Ax to recover the actual signals x, which is repeated 656 at each sub-pixel location, for all CCD pixels. As a result, a high spatial resolution image 658 without aliasing can be obtained from SAO, despite using PFOV smaller than the extent (w) of the detected area for selective excitation in SAO.

Note that "unfolding" as explained herein can also be used to improve the SAO image reconstruction quality even when PFOV larger than or equal to the extent (w) of the detected area is used for selective excitation in SAO. In conventional SAO, the reconstructed pixels are simply cropped (to the width being p) and stitched together. This way of "crop and stitch" still does not undo the apodization caused by the weighting function w(x). In contrast, "unfolding" may be used according to the present invention even when PFOV larger than or equal to the extent (w) of the detected area is used for selective excitation in SAO such that no aliasing occurs. Since the unfold process is fundamentally undoing (i.e., unapodizing) the weighting function w(x), the "unfold" process can also be used to improve image reconstruction even when PFOV>=w is used for SAO selective excitation.

Figure 7A:
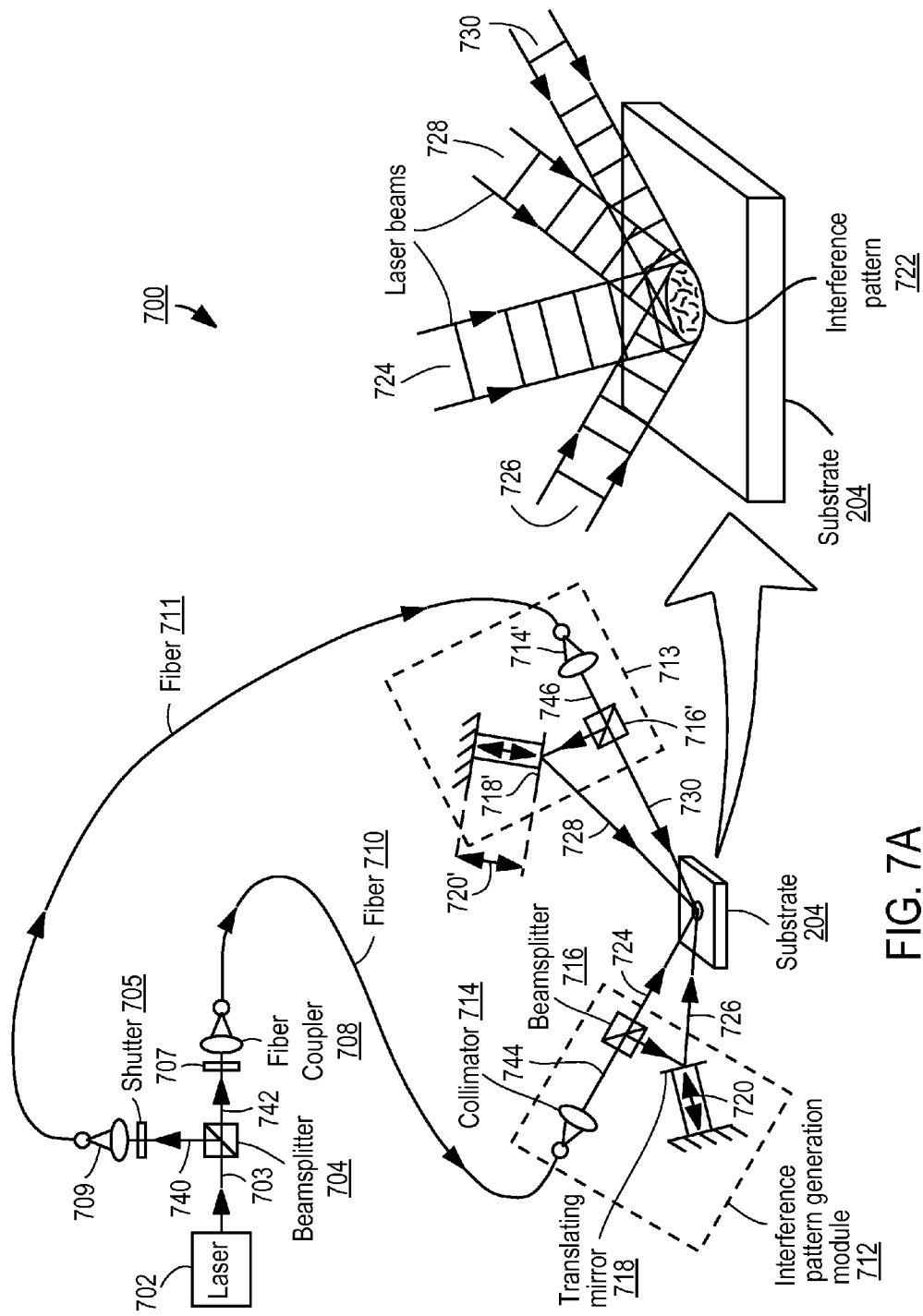
FIG. 7A illustrates a structured illumination apparatus for selectively exciting the microparticles, according to one embodiment.

FIG. 7A illustrates a structured illumination apparatus for selectively exciting the microparticles, according to one embodiment. The illumination apparatus shown in FIG. 7A is merely exemplary, and various modifications may be made to the configuration of the illumination apparatus for SAO according to the present invention. The example illumination apparatus in FIG. 7A shows only two interference pattern generation modules (IPGM) 712, 713 for simplicity of illustration, but for real DNA sequencing applications there would be a larger number of IPGMs. Each IPGM is in modular form and is configured to generate one selective excitation pattern at a given pitch and orientation, corresponding to one conjugate pair of the k-space sampling points. Thus, there is a one-to-one relationship between an IPGM and a 2-D sinusoid selective excitation pattern at a given pitch and orientation and to one conjugate pair of the k-space sampling points. A larger number (N) of selective excitation patterns would require a larger number of IPGMs in the SAO illumination apparatus.

The structured illumination apparatus 700 generates multiple mutually-coherent laser beams, the interference of which produces interference patterns. Such interference patterns are projected onto the microparticle array substrate 204 and selectively excite the DNA microparticles 202. Using the interference of multiple laser beams to generate the interference patterns is advantageous for many reasons. For example, this enables high-resolution excitation patterns with extremely large FOV and DOF. Although the structured illumination apparatus of FIG. 7A is described herein with the example of generating excitation patterns for DNA microparticles, it should be noted that the structured illumination apparatus of FIG. 7A can be used for any other type of application to generate excitation patterns for imaging any other type of target.

Referring to FIG. 7A, the structured illumination apparatus 700 includes a laser 702, a beam splitter 704, shutters 705, 707, fiber couplers 708, 709, a pair of optical fibers 710, 711, and a pair of interference pattern generation modules (IPGMs) 712, 713. As explained above, each IPGM 712, 713 generates an interference pattern (selective excitation pattern) that corresponds to one conjugate pair of k-space sampling points. The beam 703 of the laser 702 is split by the beam splitter 704 into two beams 740, 742. A pair of high-speed shutters 705, 707 is used to switch each beam 740, 742 "on" or "off" respectively, or to modulate the amplitude of each beam 740, 742, respectively. Such switched laser beams are coupled into a pair of polarization-maintaining optical fibers 711, 710 via fiber couplers 709, 708. Each fiber 711, 710 is connected to a corresponding interference pattern generation module 713, 712, respectively. The interference pattern generation module 713 includes a collimating lens 714', a beam splitter 716', and a translating mirror 718', and likewise the interference pattern generation module 712 includes a collimating lens 714, a beam splitter 716, and a translating mirror 718.

The beam 744 from the optical fiber 710 is collimated by the collimating lens 714 and split into two beams 724, 726 by the beam splitter 716. The mirror 718 is translated by an actuator 720 to vary the optical path-length of the beam 726. Thus, an interference pattern 722 is generated on the substrate 204 in the region of overlap between the two laser beams 724, 726, with the phase of the pattern changed by varying the optical path-length of one of the beams 726 (i.e., by modulating the optical phase of the beam 726 by use of the translating mirror 718).

Similarly, the beam 746 from the optical fiber 711 is collimated by the collimating lens 714' and split into two beams 728, 730 by the beam splitter 716'. The mirror 718' is translated by an actuator 720' to vary the optical path-length of the beam 728. Thus, the interference pattern 722 is generated on the substrate 204 in the region of overlap between the two laser beams 728, 730, with the pattern changed by varying the optical path-length of one of the beams 728 (i.e., by modulating the optical phase of the beam 728 by use of the translating mirror 718').

As shown in FIG. 7A, each IPGM 712, 713 is implemented in modular form according to the embodiments herein, and one IPGM produces an interference pattern corresponding to one conjugate pair of k-space points. This modularized one-to-one relationship between the IPGM and the k-space points greatly simplifies the hardware design process for SAO according to the embodiments herein. As the number of selective excitation patterns used for SAO is increased or decreased, the SAO hardware is simply changed by increasing or decreasing the number of IPGMs in a modular manner. In contrast, conventional SAO apparatuses did not have discrete interference pattern generation modules but had a series of split beams producing as many multiple interferences as possible. Such conventional way of designing SAO apparatuses produced non-optimized or redundant patterns, slowing down and complicating the operation of the SAO system.

While this implementation illustrated in FIG. 7A is used for its simplicity, various other approaches can be used within the scope of the present invention. For example, the amplitude, polarization, direction, and wavelength, in addition to or instead of the optical amplitude and phase, of one or more of the beams 724, 726, 728, 730 can be modulated to change the excitation pattern 722. Also, the structured illumination can be simply translated with respect to the microparticle array to change the excitation pattern. Similarly, the microparticle array can be translated with respect to the structured illumination to change the excitation pattern. Also, various types of optical modulators can be used in addition to or instead of the translating mirrors 718, 718', such as acousto-optic modulators, electro-optic modulators, a rotating window modulated by a galvanometer and micro-electro-mechanical systems (MEMS) modulators. In addition, although the structured illumination apparatus of FIG. 7A is described herein as using a laser 702 as the illumination source for coherent electro-magnetic radiation, other types of coherent electro-magnetic radiation sources such as an SLD (super-luminescent diode) may be used in place of the laser 702.

Also, although FIG. 7A illustrates use of four beams 724, 726, 728, 730 to generate the interference pattern 722, larger number of laser beams can be used by splitting the source laser beam into more than two beams. For example, 64 beams may be used to generate the interference pattern 722. In addition, the beam combinations do not need to be restricted to pair-wise combinations. For example, three beams 724, 726, 728, or three beams 724, 726, 730, or three beams 724, 728, 730, or three beams 726, 729, 730, or all four beams 724, 726, 728, 730 can be used to generate the interference pattern 722. Typically, a minimal set of beam combinations (two beams) is chosen as necessary to maximize speed. Also, the beams can be collimated, converging, or diverging. Although different from the specific implementations of FIG. 7A and for different applications, additional general background information on generating interference patterns using multiple beam pairs can be found in (i) U.S. Pat. No. 6,016,196, issued on Jan. 18, 2000 to Mermelstein, entitled "Multiple Beam Pair Optical Imaging," (ii) U.S. Pat. No. 6,140,660, issued on Oct. 31, 2000 to Mermelstein, entitled "Optical Synthetic Aperture Array," and (iii) U.S. Pat. No. 6,548,820, issued on Apr. 15, 2003 to Mermelstein, entitled "Optical Synthetic Aperture Array," all of which are incorporated by reference herein.

Figure 7B:
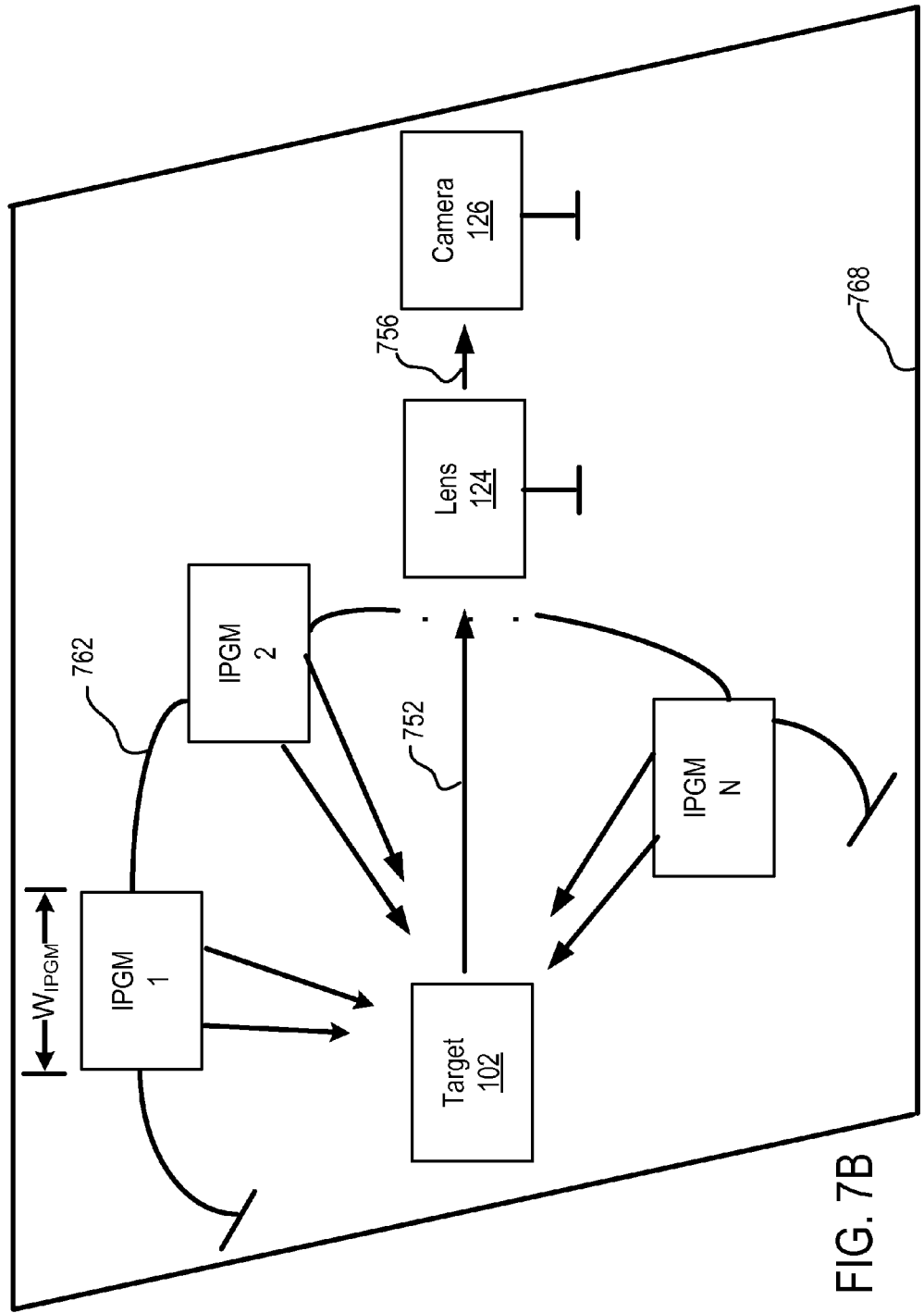
FIG. 7B illustrates the arrangement of the illumination pattern generation modules in a half-ring structure, according to one embodiment.

FIG. 7B illustrates the arrangement of the illumination pattern generation modules in a half ring structure according to one embodiment. Referring to FIG. 7B, multiple IPGMs (IPGM 1, IPGM 2, . . . , IPGM N) such as IPGMs 712, 713 (FIG. 7A) are arranged substantially symmetrically in a half-ring shape on a half-ring shaped, monolithic structure 762, to generate the selective excitation patterns. The half-ring structure 762 is fixed on the system table 768. In the embodiment of FIG. 7B, the N IPGMs generate N selective excitation patterns for SAO on the imaging target 102, and the scattered or fluoresced light 752 is passed through objective lens 124 and captured 756 by camera 126 which may be a CCD camera.

These arrangements of the IPGMs in the embodiment of FIG. 7B enable a monolithic and compact holding structure that has multiple benefits for enabling the SAO system to be used for DNA sequencing applications, compared to conventional optical-bench SAO systems where each optical component is individually mounted on its holding structure. The monolithic structure 762 enables the IPGM arrangement to be compact and symmetric, and this compact, symmetric, and monolithic structure preserves more stable channel-to-channel and beam-to-beam geometry against mechanical and thermal distortions. The compact monolithic structure 762 is also less susceptible to non-flatness or torsional and bending modes of the optical table 768, and the symmetric arrangement of the IPGMs around the half-ring structure 762 makes the effect of heat contraction or expansion less detrimental to the beam geometry, i.e., the channel-to-channel or beam-to-beam angles of laser beams are changed less compared to a non-symmetric structure. Furthermore, the compact design shortens the travel distances of the laser beam in air, making it easy to prevent air disturbances affecting the stability of the interference pattern that may cause the effective optical path length to change resulting in change of the interference fringe position. Such stability allows more accurate calibration of the beam geometry. Furthermore, the half-ring arrangement of the IPGMs in FIG. 7B has the additional advantage that it enables the imaging module (i.e., camera 126 and objective lens 124), illumination structure (i.e., the half-ring 762), and the imaging target 102 to be placed on one stiff structure (e.g., optical table) 768.

Figure 7C:
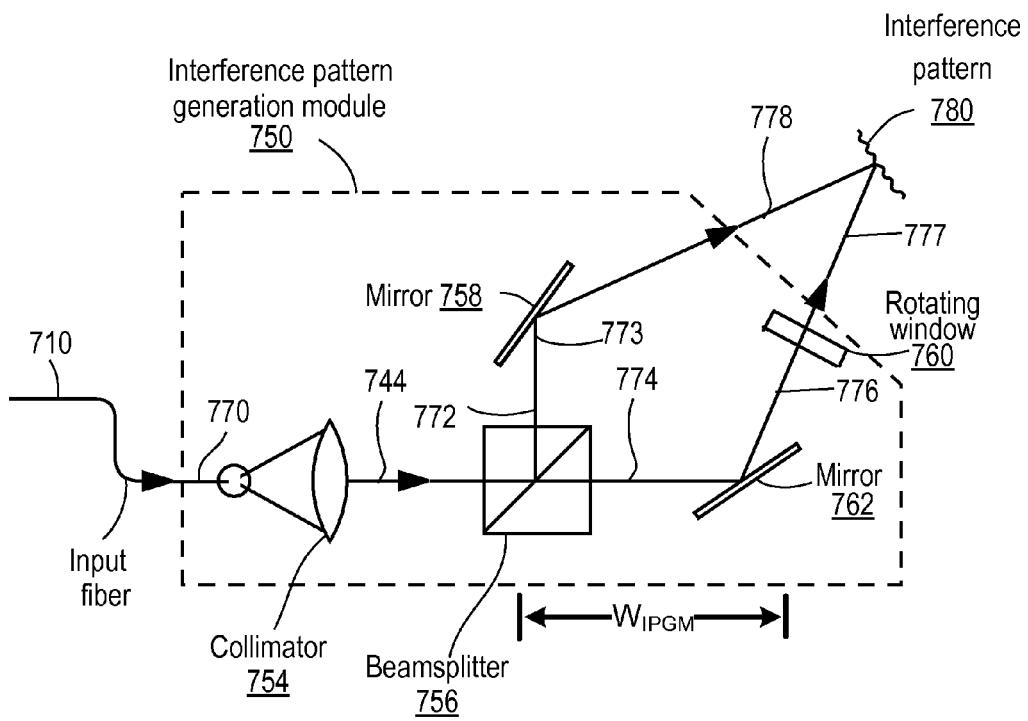
FIG. 7C illustrates the internal structure of an illumination pattern generation module, according to one embodiment.
Figure 7D:
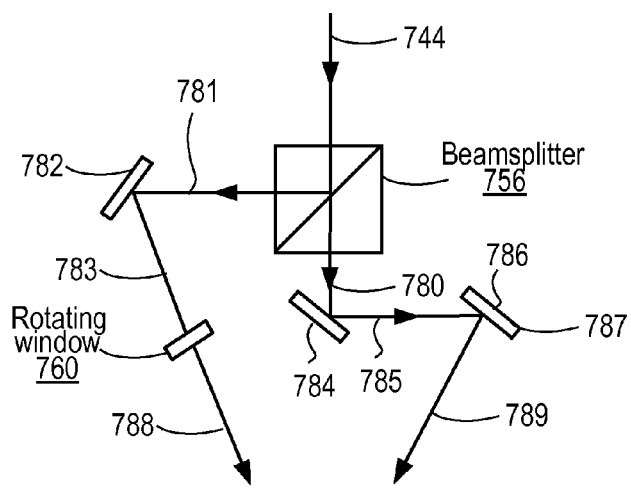
FIG. 7D illustrates the internal structure of an illumination pattern generation module, according to another embodiment.

FIG. 7C illustrates the internal structure of an illumination pattern generation module, according to one embodiment. The embodiment of FIG. 7C has a rotating window 760 in IPGM 750 that is placed after the mirror 762. The beam 770 from the optical fiber 710 is collimated by the collimating lens 754 and the collimated beam 744 is split into two beams 773, 774 by the beam splitter 756. Beam 773 is reflected by mirror 758 and the reflected beam 778 is projected onto the imaging target to generate the interference pattern 780. Beam 774 is reflected by mirror 762 and the optical path-length of the reflected beam 776 is modulated by optical window 760 that is rotated, using a galvanometer, thereby modulating the optical phase of the corresponding beam 776 and generating a modulated beam 777. The interference pattern 780 is generated in the region of overlap between the two laser beams 777, 778, with the pattern changed by varying the optical path-length of one of the beams 777. By placing the rotating window 760 after the mirror 762, the width $W_{IPGM}$ and the size of IPGM 750 can be reduced, as compared to the embodiment of FIG. 7A and FIG. 7D illustrated below. Thus, the half-ring shaped structure 762 holding the IPGMs can be made more compact, since the width $W_{IPGM}$ of the IPGM directly affects the radius of the half-ring, for example, as shown in FIG. 7B.

FIG. 7D illustrates the internal structure of an illumination pattern generation module, according to another embodiment. IPGMs in the embodiments of FIGS. 7A and 7C may produce two beams that do not have equal path length between the interfering point at the imaging target and the splitting point (i.e., the beam splitter). The non-equal path length may significantly reduce the sinusoidal contrast if a relatively short coherent-length laser is used and also limit the applicability of the SAO system to only a specific wavelength (e.g., 532 nm green laser) since only a small number of lasers with specific wavelengths have a sufficiently long coherent-length that can be used with such non-equal-path IPGMs for good sinusoidal contrast. Compared to the embodiment of FIG. 7A, the embodiment of FIG. 7D uses additional folding mirrors to achieve equal paths between the two split beams. The laser beam 744 is split into beams 781, 780 by beam splitter 756. Beam 781 is reflected by mirror 782 and its optical path-length is modulated by rotating window 760 to generate beam 788. On the other hand, beam 780 is reflected twice by two mirrors 784, 787 to generate the reflected beam 789. Beam 788 and 789 eventually interfere at the imaging target to generate the selective excitation patterns. By use of two mirrors 784, 786, the optical path 744-780-785-789 is configured to have a length substantially equal to the length of the optical path 781-783-788. This equal-path scheme allows lasers with short coherent lengths to be used to generate interference patterns with high contrast. Moreover, this equal-path scheme enables the SAO system to be used with wavelengths other than 532 nm, thus making multiple-color SAO practical.

Upon reading this disclosure, those of skill in the art will appreciate still additional alternative structural and functional designs for a method and an apparatus for synthetic aperture optics. Thus, while particular embodiments and applications of the present invention have been illustrated and described, it is to be understood that the invention is not limited to the precise construction and components disclosed herein and that various modifications, changes and variations which will be apparent to those skilled in the art may be made in the arrangement, operation and details of the method and apparatus of the present invention disclosed herein without departing from the spirit and scope of the invention as defined in the appended claims.

What is claimed is:

1. A method for performing synthetic aperture optics (SAO) on a target including one or more objects, the method comprising the steps of:

illuminating the target with a predetermined number (N) of selective excitation patterns, wherein the set of N selective excitation patterns results from a design process using a minimum distance ($\Delta x$) between objects to be resolved by SAO and a width of a detected area (w) captured by a pixel of a system for said optical imaging, wherein the number (N) of selective excitation patterns is substantially determined from:

N=floor(L/2)

wherein L is the number of k-space sample points in the k-space, and floor ( ) rounds the number to the nearest but smaller integer; and L=round((PFOV/Δx)²)

wherein round ( ) rounds the number to the nearest integer, and PFOV is the extent in the reciprocal space of the k-space to be reconstructed from the samples;

optically imaging the illuminated target at a resolution insufficient to resolve the objects; and processing optical images of the illuminated target using information on the selective excitation patterns to obtain a final image of the illuminated target at a resolution sufficient to resolve the objects.

2. The method of claim 1, wherein the number (N) of selective excitation patterns corresponds to the number of k-space sampling points in a k-space sampling space in a frequency domain, an extent of the k-space sampling space being substantially proportional to an inverse of the minimum distance (Δx) between the objects that is to be resolved by SAO, and an inverse of a k-space sampling interval between the k-space sampling points being less than the width of a detected area (w) captured by a pixel of a system for said optical imaging.

3. The method of claim 2, further comprising removing aliasing in the final image caused as a result of using said inverse of the k-space sampling interval less than the width of the detected area (w) captured by the pixel of said optical imaging system.

4. The method of claim 1, further comprising removing effects of apodization caused by a weighting function of a system for said optical imaging, said weighting function corresponding to a convolution of a pixel sensitivity function of a pixel of said optical imaging system for detecting light from the illuminated target and a point-spread function of a lens through which said light is passed through in said optical imaging system.

5. The method of claim 1, wherein the number (N) of selective excitation patterns is determined based upon at least one of a plurality of parameters of a system for said optical imaging, including a width (w) of a detected area captured by a pixel of said optical imaging system, a wavelength of light from the illuminated target, and a numerical aperture of a lens through which said light is passed through in said optical imaging system.

6. The method of claim 1, wherein the number (N) of selective excitation patterns corresponds to non-uniformly selected ones of the k-space sampling points.

7. The method of claim 1, wherein the target is illuminated with two phases of each one of the selective excitation patterns and another phase of only one of the selective excitation patterns, said another phase being different from the two phases.

8. The method of claim 1, wherein the target is illuminated with three phases of each one of the selective excitation patterns.

9. The method of claim 1, wherein the objects include nucleic acid microparticles.

10. A system for performing synthetic aperture optics (SAO) on a target including one or more objects, the system comprising:

a plurality of illumination modules configured to illuminate the target with a predetermined number (N) of selective excitation patterns, wherein the set of N selective excitation patterns results from a design process using a minimum distance (Δx) between objects to be resolved by SAO and a width of a detected area (w) captured by a pixel of a system for said optical imaging, wherein the number (N) of selective excitation patterns is substantially determined from:

N=floor(L/2)

wherein L is the number of k-space sample points in the k-space, and floor ( ) rounds the number to the nearest but smaller integer; and L=round((PFOV/Δx)²)

wherein round ( ) rounds the number to the nearest integer, and PFOV is the extent in the reciprocal space of the k-space to be reconstructed from the samples;

an optical imaging module configured to optically image the illuminated target at a resolution insufficient to resolve the objects; and a SAO processing module configured to process the optical images of the illuminated target using information on the selective excitation patterns to obtain a final image of the illuminated target at a resolution sufficient to resolve the objects.

11. The system of claim 10, wherein the number (N) of selective excitation patterns corresponds to the number of k-space sampling points in a k-space sampling space in a frequency domain, an extent of the k-space sampling space being substantially proportional to an inverse of the minimum distance (Δx) between the objects that is to be resolved by SAO and an inverse of a k-space sampling interval between the k-space sampling points being less than the width of a detected area (w) captured by a pixel of the optical imaging module.

12. The system of claim 11, wherein the SAO processing module is further configured to remove aliasing in the final image caused as a result of using said inverse of the k-space sampling interval less than the width of the detected area (w) captured by the pixel of the optical imaging module.

13. The system of claim 10, wherein the SAO processing module is further configured to remove effects of apodization caused by a weighting function of the optical imaging module, said weighting function corresponding to a convolution of a pixel sensitivity function of a pixel of said optical imaging module for detecting light from the illuminated target and a point-spread function of a lens through which said light is passed through in said optical imaging module.

14. The system of claim 10, wherein the number (N) of selective excitation patterns is determined based upon at least one of a plurality of parameters of said optical imaging module, including a width (w) of a detected area captured by a pixel of said optical imaging module, a wavelength of the light from the illuminated target, and a numerical aperture of a lens through which said light is passed through in said optical imaging module.

15. The system of claim 10, wherein the number (N) of selective excitation patterns corresponds to non-uniformly selected ones of the k-space sampling points.

16. The system of claim 10, wherein the target is illuminated with two phases of each one of the selective excitation patterns and another phase of only one of the selective excitation patterns, said another phase being different from the two phases.

17. The system of claim 10, wherein the target is illuminated with three phases of each one of the selective excitation patterns.

18. The system of claim 10, wherein the objects include nucleic acid microparticles.

19. The system of claim 10, wherein each illumination module generates one of the selective excitation patterns for illuminating the target.

20. The method of claim 1, wherein N=12 and L=25.

21. The method of claim 1, further comprising further reducing the number of k-space sampling points.

22. The method of claim 21, wherein the number (N) of selective excitation patterns corresponds to sparse k-space sampling points.

23. The method of claim 1, wherein the selective excitation patterns correspond to the k-space sampling points within a circular region.

24. The system of claim 10, wherein N=12 and L=25.

25. The system of claim 10, wherein the number of k-space sampling points is further reduced.

26. The system of claim 25, wherein the number (N) of selective excitation patterns corresponds to sparse k-space sampling points.

27. The system of claim 10, wherein the selective excitation patterns correspond to the k-space sampling points within a circular region.

\* \* \* \* \*